SURGERY
128-89.A
35
21 A
Examiner's Initials

No. 12,794. REISSUED MAY 19, 1908.

P. STUKEY. D.D.S.

DEVICE FOR REPAIRING FRACTURED JAWS.

APPLICATION FILED APR. 14, 1908.

Witnesses:
[illegible]
[illegible]

Inventor:
Peter Stukey,
by Ferrier & Ferrier,
attys

THE NORRIS PETERS CO., WASHINGTON, D. C.

28. SURGERY.

9

Examiners' Room

UNITED STATES PATENT OFFICE.

PETER STUKEY, OF AUBURN, INDIANA.

DEVICE FOR REPAIRING FRACTURED JAWS.

No. 12,794. Specification of Reissued Letters Patent. Reissued May 19, 1908.

Original No. 878,577, dated February 11, 1908, Serial No. 365,408. Application for reissue filed April 14, 1908. Serial No. 427,328.

*To all whom it may concern:*

Be it known that I, PETER STUKEY, D. D. S., a citizen of the United States, residing at Auburn, in the county of Dekalb and State of Indiana, have invented a new and useful Article Known as a Device for Repairing Broken or Fractured Jaws, of which the following is a specification.

This invention relates to devices to be used in repairing broken or fractured jaws, and has for its object to provide a simple and efficient means for holding a jaw bone (which has been properly set after being fractured,) in its set condition, while at the same time permitting the normal movement of the jaws in eating and speaking.

Heretofore it has been necessary in cases where a broken jaw was treated, to bind the jaws together, so as to preserve the set condition. Accordingly, the patient would be unable to speak or to masticate, and in order to feed him it has been necessary to remove one of the front teeth and inject liquid food. By the use of my device as aforesaid the patient may move the jaws in a vertical way as much as desired, enabling him to eat and speak with impunity, while at the same time preserving the broken jaw or jaws in their set condition and preventing a movement of the fractured parts with relation to each other.

Figure 1:
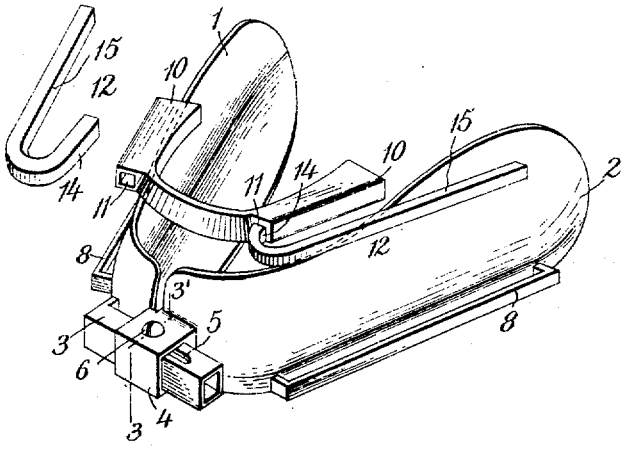
Figure 2:
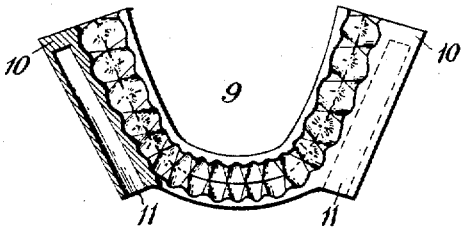
Figure 3:
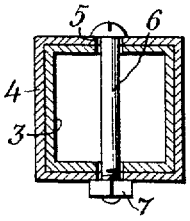

In the accompanying drawings, which are to be taken as a part of this specification, and in which I have shown a merely preferred form of embodiment of the invention, Figure 1 is a collective view of the various parts of my device, as applied to a lower jaw; Fig. 2 is a bottom plan view of the rubber plate which must be made for each case; and Fig. 3 is a section on line 3—3 of Fig. 1.

Referring to the numerals on the drawings, 1 and 2 indicate a pair of splints or supports for the inferior maxillary bone having a proper inside contour, and adapted when assembled as shown in Fig. 1 to closely surround the lower jaw. These members may be made of any preferred material, as for instance, aluminum, and they are provided at the forward ends, which inclose the chin, with means for adjustably connecting them together, as for instance, a telescoping connection comprising a box-lug 3′ rigidly attached to the splint 1 and slidable in a sleeve 4 secured to the splint 2. A slot 5 extends entirely through the lug 3′, through which is adapted to pass a securing bolt 6 mounted in alined apertures in the sleeve 4 and provided with a nut 7. Each of the splints 1 and 2 is provided at its sides with a securing rail, for a purpose hereinafter referred to. It will be evident that by a proper manipulation of the connection between the splints they may be made to fit lower jaws of various sizes within limits.

As a splint for the inside of the lower jaw, and adapted to coöperate with the splints 1 and 2 I provide a plate 9, which must be made separately for each individual case, and is preferably formed of rubber placed against the lower teeth while in a plastic condition and allowed to harden in position. The said plate is provided at each side with a laterally extending portion 10 provided with a longitudinally extending squared aperture 11, whose orifice is toward the front of the plate, so that when in use, as shown in Fig. 1, the opening of said aperture will be at or near the front teeth. Removably secured in said apertures 11 are a pair of substantially U-shaped members 12, having a short arm 14 adapted to extend into the apertures 11 and shaped conformably therewith, and a long arm 15 adapted to extend along the side of the plate 9.

In use the plate being in position as before described, and the members 12 inserted in the respective apertures 11 the long arms 15 will extend outside the cheek of the patient. The splints 1 and 2 being now properly fitted and positioned on the lower jaw, the long arms 15 respectively are securely tied to the securing rails 8 on each side as by means of a suitable wire or the like and the lower jaw is thus rigidly held in its set condition.

In cases of fracture to the upper jaw, the plate 9 is molded to the upper teeth, and the arms 15 of the U-shaped members are connected by means of fastenings extending from one to the other over the top of the head. In such cases it is preferable to rigidly secure the U-shaped members within the apertures 11 as by cementing them therein, and this practice may also be followed in connection with the use of the plate on the lower jaw.

What I claim is:—

1. In a device of the character described, in combination, a two-part splint member for the outside surface of a jaw-bone, comprising two members adjustably secured together at one end, and each provided with a securing rail, and a plate fitting against the teeth of said jaw, having attaching members secured thereto, adapted to be connected with said securing rails, substantially as and for the purpose set forth.

2. In a device of the character described, the combination of a splint for the outside surface of a lower jaw-bone, and a splint for the inside surface of said jaw-bone comprising a plate provided with longitudinal apertures, and attaching members adapted to be removably held in said apertures.

3. In a device of the character described, the combination of a splint for the outside surface of a lower jaw-bone, and a splint for the inside surface of said jaw-bone comprising a plate provided with squared longitudinal apertures, and attaching members adapted to be removably held in said apertures.

4. In a device of the character described, an adjustable splint for the outside surface of a lower jaw-bone, and a splint for the inside surface of said jaw-bone, secured together, said outside splint comprising two members connected at one end by a telescoping connection.

5. A splint for the inner surface of a jaw-bone comprising a plate shaped conformably to said surface, and attaching members removably secured to said plate.

PETER STUKEY.

Witnesses:
CLARA WUERTHNER STUKEY,
W. C. CRAMAR.